(12) United States Patent
Zheng et al.

(10) Patent No.: US 10,948,431 B1
(45) Date of Patent: Mar. 16, 2021

(54) VISIBLE TEST SYSTEM AND ROCK MASS HEATING METHOD

(71) Applicant: INSTITUTE OF GEOLOGY AND GEOPHYSICS, CHINESE ACADEMY OF SCIENCES, Beijing (CN)

(72) Inventors: Bo Zheng, Beijing (CN); Xiao Li, Beijing (CN); Shouding Li, Beijing (CN); Jianming He, Beijing (CN); Zhaobin Zhang, Beijing (CN); Tianqiao Mao, Beijing (CN); Guanfang Li, Beijing (CN); Pengfei He, Beijing (CN); Yanfang Wu, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/096,964

(22) Filed: Nov. 13, 2020

(30) Foreign Application Priority Data

Oct. 9, 2020 (CN) .......................... 202011071854.0

(51) Int. Cl.
*G01N 23/04* (2018.01)
*G01N 33/24* (2006.01)
(Continued)

(52) U.S. Cl.
CPC ........... *G01N 23/046* (2013.01); *G01K 1/026* (2013.01); *G01N 33/24* (2013.01); *H05B 3/48* (2013.01); *H05B 6/10* (2013.01); *G01N 2223/1016* (2013.01); *G01N 2223/309* (2013.01); *G01N 2223/311* (2013.01);
(Continued)

(58) Field of Classification Search
None
See application file for complete search history.

(56) References Cited

U.S. PATENT DOCUMENTS

| 5,297,420 A | * | 3/1994 | Gilliland ................ G01N 15/08 73/38 |
| 9,903,826 B2 | * | 2/2018 | Alshehri .......... G01N 23/20025 |

(Continued)

*Primary Examiner* — Thomas R Artman
(74) *Attorney, Agent, or Firm* — Bayramoglu Law Offices LLC

(57) ABSTRACT

A visible test system includes a test chamber system, a heating system, a pressure control system, and a high-energy accelerator CT detection system configured to scan and detect the seepage and migration of magnetic fluid in fractures in a sample. The test chamber system includes a pressure chamber and a sample encapsulation device immersed in hydraulic oil arranged inside the pressure chamber. The heating system includes a magnetic fluid heating device, a resistance wire heating device and a temperature detection device. The magnetic fluid heating device includes a magnetic fluid loading pump configured to supply the magnetic fluid injected into the sample encapsulation device and an alternating magnetic field control device configured to provide an alternating magnetic field for heating the magnetic fluid. The resistance wire heating device is configured to heat the hydraulic oil. The present invention makes the fracture connectivity change during rock mass fracture visible.

17 Claims, 4 Drawing Sheets

(51) Int. Cl.
  *H05B 6/10*     (2006.01)
  *H05B 3/48*     (2006.01)
  *G01N 23/046*   (2018.01)
  *G01K 1/02*     (2021.01)

(52) U.S. Cl.
  CPC ............ *G01N 2223/3106* (2013.01); *G01N 2223/319* (2013.01); *G01N 2223/3306* (2013.01); *G01N 2223/3307* (2013.01); *G01N 2223/419* (2013.01); *G01N 2223/616* (2013.01)

(56) References Cited

U.S. PATENT DOCUMENTS

| | | | |
|---|---|---|---|
| 10,139,355 B1* | 11/2018 | Li | G01N 33/24 |
| 10,234,407 B2* | 3/2019 | Li | G01N 23/046 |
| 10,697,295 B2* | 6/2020 | Buono | G01V 3/32 |
| 2016/0077023 A1* | 3/2016 | Alshehri | G01N 23/046 378/20 |
| 2018/0258763 A1* | 9/2018 | King, Jr. | G01N 23/046 |
| 2018/0259467 A1* | 9/2018 | Buono | E21B 49/02 |
| 2018/0306736 A1* | 10/2018 | Li | G01N 1/38 |

\* cited by examiner

VISIBLE TEST SYSTEM AND ROCK MASS HEATING METHOD

CROSS REFERENCE TO THE RELATED APPLICATIONS

This application is based upon and claims priority to Chinese Patent Application No. 202011071854.0, filed on Oct. 9, 2020, the entire contents of which are incorporated herein by reference.

TECHNICAL FIELD

The present invention belongs to the field of geotechnical engineering tests, and more particularly, relates to a visible test system and a rock mass heating method.

BACKGROUND

In the process of shale oil and gas exploitation, the geological make-up of the reservoir must be reconstructed to maximize capture of oil and gas resources. During the reconstruction, it is desirable that pores and fractures be connected to make optimal oil and gas migration channels, which results in extraction efficiencies. When simulating high-temperature conditions of rock mass, current simulation tests typically use three heating methods. The first heating method locates the pressure chamber inside a temperature control facility. Instruments are placed in a high-temperature environment and connected with a temperature control device to achieve the temperature required for the test. Although this method means that instruments need not be developed, it is expensive to establish a temperature control laboratory. In this regard, the test environment is generally less than ideal, and instrument components are required to have high-temperature resistance and they eventually fail and need replacing. The second heating method uses heating coils, tubes, rods, and plates to heat the fluid inside the pressure chamber, whereby the fluid is directly heated to obtain the desired test temperature. This method, however, is difficult to uniformly heat the liquid in the pressure chamber under confining high pressures. As a result, the interior of the rock soil sample may be unevenly heated, thus producing unsatisfactory test conditions and unreliable simulated test data. The third heating method adopts a heating mode outside the pressure chamber. In this method, a coil is wound outside the pressure chamber, and the fluid in the pressure chamber is heated by heating the coil. Since the temperature of the liquid in the pressure chamber is increased by heat transfer through an outer cover, it takes a long time for the sample to reach the desired test temperature. The properties of rock soil change under different temperatures, and heating reduces the viscosity of the pore water in the sample, which in turn, increases the permeability coefficient and induces the thermal expansion of the pore water and soil particles making the soil sample prone to increase in volume. Therefore, under this method consideration must be given to the several variable affected by the influence of temperature during the test. Hence, the aforementioned three heating methods of prior temperature control test devices have their respective shortcomings.

In the process of deep underground oil and gas capture and exploitation, deep underground reservoirs must be reconstructed to fracture the rock in the reservoir, increase the connectivity of the fractures and improve the migration efficiency of oil and gas in the reservoir. Because the impact of reservoir reconstruction thousands of meters underground cannot be seen, the only feasible research method is indoor rock high-temperature and high-pressure simulation testing. Therefore, it is desirable to develop an improved indoor testing device. Such a device should be capable of not only uniformly heating the interior and exterior of the rock mass, but also obtaining real-time propagation and development states of fractures and pores inside the rock mass.

SUMMARY

In order to solve the above-mentioned problems in the prior art, that is, to solve the problem that current simulation test methods and devices cannot realize uniform heating of the rock mass sample and visible detection of the propagation process of fractures inside the pressurized sample is not possible, the present invention provides a test system and rock mass heating method that allows for uniform heating of rock and visualization of its impact on the propagation of fractures.

The first aspect of the present invention provides a visible simulated test system. The system includes a high-energy accelerator computed tomography (CT) detection system, a test chamber system, a heating system, and a pressure control system. The high-energy accelerator CT detection system is configured to scan and detect the seepage and migration of magnetic fluid in fractures in a sample.

The test chamber system includes a pressure chamber and a sample encapsulation device, and the sample encapsulation device is immersed in hydraulic oil arranged inside the pressure chamber.

The heating system includes a magnetic fluid heating device, a resistance wire heating device and a temperature detection device. The temperature detection device is configured to detect temperatures of different positions in the pressure chamber. The magnetic fluid heating device includes a magnetic fluid loading pump and an alternating magnetic field control device. The magnetic fluid loading pump is configured to supply the magnetic fluid injected into the sample encapsulation device. The alternating magnetic field control device is configured to provide an alternating magnetic field for heating the magnetic fluid. The resistance wire heating device is configured to heat the hydraulic oil inside the pressure chamber to heat the sample inside the sample encapsulation device.

The pressure control system includes an axial pressure control device and a confining pressure control device. The axial pressure control device is configured to provide an axial pressure for the sample inside the sample encapsulation device, and the confining pressure control device is configured to provide a peripheral pressure for the sample inside the sample encapsulation device.

In some preferred embodiments, the sample encapsulation device includes an upper spacer block, a first permeable spacer block, a second permeable spacer block, a lower spacer block and a heat shrinkable tube. The first permeable spacer block and the upper spacer block are sequentially arranged above the sample. The second permeable spacer block and the lower spacer block are sequentially arranged under the sample. The heat shrinkable tube is arranged outside the first permeable spacer block, the sample, and the second permeable spacer block. The length of the heat shrinkable tube is greater than the distance between the first permeable spacer block and the second permeable spacer block.

In some preferred embodiments, an adjusting spherical hinge and a pressure sensor are sequentially arranged above the sample encapsulation device. The adjusting spherical hinge is configured to adjust the unevenness of the upper and lower end surfaces of the sample. The pressure sensor is configured to detect an axial force acting on the sample under a load applied by the axial pressure control device.

In some preferred embodiments, the resistance wire heating device is arranged under the sample encapsulation device.

The resistance wire heating device includes a resistance wire heating controller and a resistance wire heating spacer block. The resistance wire heating spacer block includes an upper heating spacer block, a thermal resistance wire and a lower heating spacer block. The area of the upper heating spacer block is larger than the area of the lower spacer block. The thermal resistance wire is arranged between the upper heating spacer block and the lower heating spacer block, and is connected to the resistance wire heating controller via a wire.

In some preferred embodiments, a magnetic fluid injection hole is formed on a side of the upper spacer block, and a first magnetic fluid channel in fluid communication with the magnetic fluid injection hole and the first permeable spacer block is arranged inside the upper spacer block.

A magnetic fluid discharge hole is formed on a side of the lower spacer block, and a second magnetic fluid channel in fluid communication with the magnetic fluid discharge hole and the second permeable spacer block is arranged inside the lower spacer block.

The upper spacer block is in fluid communication with the magnetic fluid loading pump through a magnetic fluid injection pipeline, so that the magnetic fluid is injected into the sample. The lower spacer block is in fluid communication with the magnetic fluid loading pump through a magnetic fluid discharge pipeline, so that the magnetic fluid inside the sample is discharged.

In some preferred embodiments, the pressure chamber includes a pressure chamber end cover, a pressure chamber cylinder, and a pressure chamber base. The pressure chamber end cover is hermetically arranged at the upper end opening of the pressure chamber cylinder, and the pressure chamber base is hermetically arranged at the lower end opening of the pressure chamber cylinder. The pressure chamber end cover, the pressure chamber cylinder, the pressure chamber base, and the hydraulic oil arranged inside the pressure chamber cylinder constitute the confining pressure control device.

The axial pressure control device is arranged under the pressure chamber base, and the axis of the axial pressure control device overlaps with the axis of the sample encapsulation device.

In some preferred embodiments, the axial pressure control device includes a loading cylinder. The loading cylinder includes a loading cylinder end cover, a loading cylinder block, a loading cylinder piston and a loading cylinder base. The loading cylinder end cover is fixedly arranged under the pressure chamber base, the loading cylinder piston is arranged inside the loading cylinder block, and the loading cylinder piston penetrates the pressure chamber base.

In some preferred embodiments, the alternating magnetic field control device includes an alternating magnetic field controller and an alternating magnetic field generator. The alternating magnetic field controller is in communication connection with the alternating magnetic field generator and is configured to control the intensity and frequency of a magnetic field in the alternating magnetic field generator.

The alternating magnetic field generator includes a plurality of magnetic cores, a supporting base, and a coil wound around the magnetic core. The supporting base is fixedly arranged on the top of the pressure chamber base. The plurality of magnetic cores are arranged in an array configuration around the sample encapsulation device. The magnetic core is fixedly arranged on the upper part of the supporting base through a connecting plate.

In some preferred embodiments, the visible test system further includes a base and a rotating bearing device. The test chamber system and the high-energy accelerator CT detection system are both arranged on the upper part of the base.

The high-energy accelerator CT detection system includes a ray source device and a detector device. The ray source device and the detector device are separately arranged on both sides of the test chamber system. The ray source device includes a ray source and a ray source stand column, and the detector device includes a detector and a detector stand column. The ray source is arranged on the base through the ray source stand column, and the detector is arranged on the base through the detector stand column. The height of each of the ray source and the detector is greater than a height of the test chamber system.

The rotating bearing device is arranged under the test chamber system and is configured to drive the test chamber system to rotate. The rotating bearing device includes a rotating table and a drag chain, and one end of the drag chain is fixedly arranged on the rotating table. A drag chain winding part is provided on the periphery of the rotating table, and the drag chain is driven by a power device of the rotating table to wind around the drag chain winding part.

The second aspect of the present invention provides a rock mass heating method, including:

step S100, encapsulating a sample by a sample encapsulation device;

step S200, constructing fluid communication between the sample and a magnetic fluid loading pump through a magnetic fluid injection pipeline, an upper spacer block, and a first permeable spacer block to form a magnetic fluid injection channel; and constructing fluid communication between the sample and the magnetic fluid loading pump through a magnetic fluid discharge pipeline, a lower spacer block, and a second permeable spacer block to form a magnetic fluid discharge channel;

activating a high-energy accelerator CT detection system to obtain a first state of the sample;

step S300, injecting hydraulic oil into a pressure chamber until the sample is hermetically encapsulated by the hydraulic oil, to form confining oil to simulate a lithostatic confining pressure;

increasing a pressure applied to the sample to a set axial pressure value by an axial pressure control device arranged in the axial direction of the sample to simulate in-situ stress;

obtaining a second state of the sample based on scanning detection of the high-energy accelerator CT detection system;

step S400, injecting the magnetic fluid into the sample in the second state through the magnetic fluid injection pipeline, and obtaining a third state of the sample based on a seepage state of the magnetic fluid inside the sample detected by the high-energy accelerator CT detection system or based on a set injection time;

step S500, heating the magnetic fluid through an alternating magnetic field generator arranged externally to heat the interior of the sample in the third state;

heating the confining oil through a resistance wire heating device provided under the sample to heat the exterior of the sample in the third state; and based on temperatures of different positions in the pressure chamber detected by a temperature detection device, uniformly heating the sample to a set target temperature.

The advantages of the present invention are as follows:

1) By means of the visible test system of the present invention, a rock soil sample is heated by the heating devices arranged inside and outside the rock soil sample in the heating system to realize uniform heating of the rock soil sample. The propagation and development states of fractures inside the rock soil under different pressures and temperatures are obtained by the high-energy accelerator CT detection system. The present invention utilizes the magnetic fluid permeating in the pores and fractures, and the density of the magnetic fluid is much greater than that of the rock soil sample, so that more reliable three-dimensional change states of the fractures inside the sample can be obtained.

2) According to the rock mass heating method of the present invention, the magnetic fluid is injected into the rock soil sample by using the heating phenomenon of the magnetic fluid in the alternating magnetic field, and then the rock soil sample is placed in the alternating magnetic field, so as to internally heat the rock and soil sample. Meanwhile, the hydraulic oil arranged around the sample is heated by the resistance wire heating device arranged outside the rock soil sample. The method based on the combination of internal heating and external heating, is first proposed to realize the high-temperature pressurization test of the rock soil, and realize the uniform heating of the rock soil as a whole, so as to obtain more reliable test simulation parameters.

3) In the present invention, the fractures that the magnetic fluid reaches are the interconnected fractures and pores, and the fractures that the magnetic fluid does not reach are disconnected fractures. An alternating magnetic field is applied around the rock during rock fracture to increase the temperature of the magnetic fluid, which not only improves the fluidity and permeability of the magnetic fluid, but also achieves the effect of heating the rock internally. At the same time, the propagation and development processes of the fractures inside the rock sample under different set parameters can be obtained. Through the simulation test of the present invention, during the shale oil and gas capture and exploitation process, the reservoir geological body can be reconstructed based on the reliable parameter data obtained by the test to obtain more connected pores and fractures in the rock, and establish more oil and gas migration channels to improve the efficiency of oil and gas resource capture and exploitation.

4) The visible test system in the present invention is properly designed and operated, for example, the heating power is convenient to adjust, the heating response time is short, and the heating power is high, which has a high degree of visualization, and can obtain reliable test parameters.

BRIEF DESCRIPTION OF THE DRAWINGS

By reading the detailed description of the non-restrictive embodiments with reference to the following drawings, other features, objectives and advantages of the present application will become more apparent.

Figure 1:
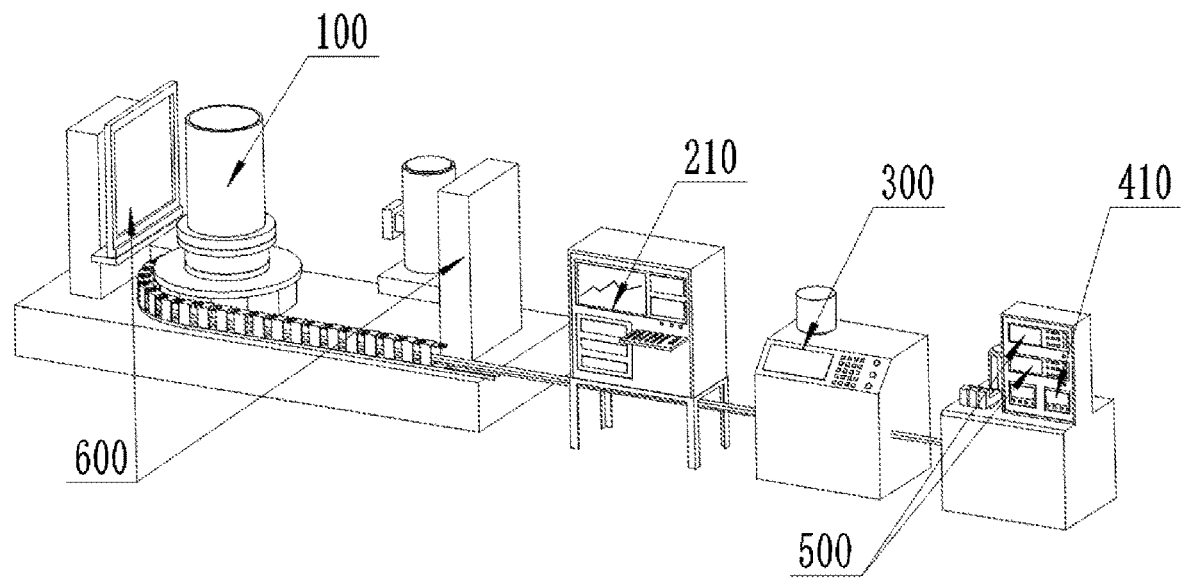
FIG. 1 is a schematic view of a three-dimensional structure of the visible test system according to an embodiment of the present invention.

DESCRIPTION OF REFERENCE NUMERALS 100, test chamber system; 110, pressure chamber; 111, pressure chamber end cover; 112, pressure chamber cylinder; 113, pressure chamber base; 120, sample encapsulation device; 121, heat shrinkable tube; 130, upper spacer block; 131, first magnetic fluid channel; 132, first thermocouple; 140, first permeable spacer block; 150, lower spacer block; 151, second magnetic fluid channel; 152, second thermocouple; 153, permeable groove; 160, second permeable spacer block; 170, sample;

210, alternating magnetic field controller; 220, alternating magnetic field generator, 221, magnetic core; 222, coil; 223, connecting plate; 224, supporting base;

300, magnetic fluid loading pump;

410, resistance wire heating controller; 420, resistance wire heating spacer block; 421, upper heating spacer block; 422, thermal resistance wire; 423, lower heating spacer block; 430, temperature detection device;

500, pressure control system; 510, axial pressure control device; 511, loading cylinder; 5111, loading cylinder piston; 5112, loading cylinder end cover; 5113, loading cylinder block; 5114, loading cylinder base; 530, top pressure sensor; 540, adjusting spherical hinge; and 600, high-energy accelerator CT detection system; 610, ray source; 611, ray source stand column; 620, detector; 621, detector stand column; 630, base; 640, drag chain; 650, rotating table.

DETAILED DESCRIPTION OF THE EMBODIMENTS

The preferred embodiments of the present invention are described below with reference to the drawings. Those skilled in the art should understand that these embodiments are only used to explain the technical principles of the present invention and are not intended to limit the scope of protection of the present invention.

The present invention will be further described below with reference to the drawings in combination with specific embodiments.

Referring to FIG. 1, a schematic view of a three-dimensional structure of the visible test system according to an embodiment of the present invention. The system includes the test chamber system 100, the heating system, the pressure control system 500 and the high-energy accelerator CT detection system 600. The high-energy accelerator CT detection system 600 is arranged on sides of the test chamber system 100 and detects the seepage, migration and diffusion path of the magnetic fluid inside the sample under different pressures and temperatures to obtain the propagation and development state as well as the connectivity of the fractures and pores in the rock mass or rock soil sample, so as to obtain the connectivity of the pores and fractures in the rock mass or rock soil under different conditions. Reliable test data is thus provided or the reconstruction of the reservoir geological body in the process of shale oil and gas capture and exploitation is realized to obtain more connected pores and fractures, establish more oil and gas migration channels and improve the oil and gas exploitation efficiency. The test chamber system 100 includes a pressure chamber and a sample encapsulation device, and the sample encapsulation device is immersed in the hydraulic oil arranged inside the pressure chamber. The heating system includes a magnetic fluid heating device, a resistance wire heating device and a temperature detection device. The temperature detection device is configured to detect the temperatures of different positions in the pressure chamber. The magnetic fluid heating device includes a magnetic fluid loading pump and an alternating magnetic field control device. The magnetic fluid loading pump is configured to supply and recover the magnetic fluid injected into the sample encapsulation device. The alternating magnetic field control device is configured to provide an alternating magnetic field for heating the magnetic fluid. The heating phenomenon of the magnetic fluid in the alternating magnetic field is utilized to achieve the purpose of heating the rock mass or rock soil sample from the interior of the sample. The resistance wire heating device is configured to heat the hydraulic oil inside the pressure chamber to heat the sample inside the sample encapsulation device, that is, heat the sample from the exterior of the sample. The pressure control system 500 includes an axial pressure control device and a confining pressure control device. The axial pressure control device is configured to provide an axial pressure for the sample inside the sample encapsulation device, and the confining pressure control device is configured to provide a peripheral pressure for the sample inside the sample encapsulation device to simulate the in-situ stress. Each of the axial pressure control device and the confining pressure control device includes a corresponding control device arranged outside the test chamber system and a sample acting device arranged inside the test chamber system.

Further, the test chamber system 100 and the high-energy accelerator CT detection system 600 are arranged on the same base to ensure the level standard of the sample in the test device and minimize the influence of external factors on the simulation test.

Further, the device inside the test chamber system is connected to the corresponding controller arranged outside the test chamber system through a corresponding cable. The cable is arranged on the lower periphery of the test chamber system, without affecting the rotation adjustment of the test chamber system and the three-dimensional visible detection of the high-energy accelerator CT detection system.

Figure 2:
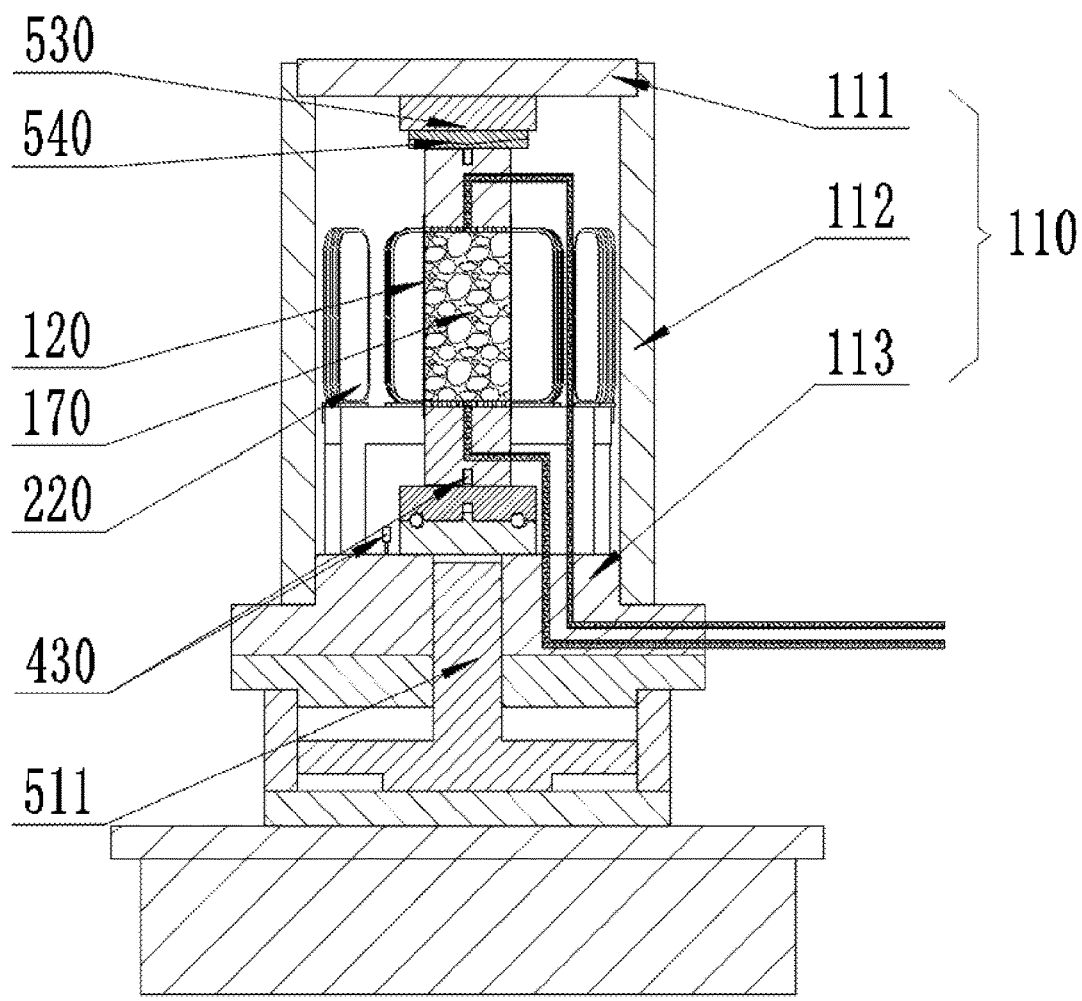
FIG. 2 is a cross-sectional view of the structure of the test chamber system in FIG. 1.

Referring to FIG. 2, a cross-sectional view of the structure of the test chamber system in FIG. 1 is shown. The pressure chamber 110 includes the pressure chamber end cover 111, the pressure chamber cylinder 112, and the pressure chamber base 113. The pressure chamber end cover is hermetically arranged at the upper end opening of the pressure chamber cylinder, and the pressure chamber base is hermetically arranged at the lower end opening of the pressure chamber cylinder. The pressure chamber end cover, the pressure chamber cylinder and the pressure chamber base constitute the sealing structure of the sample. The pressure chamber end cover, the pressure chamber cylinder, the pressure chamber base, and the hydraulic oil (not shown) arranged inside the pressure chamber cylinder constitute the confining pressure control device to simulate the confining pressure of the in-situ stress and provide a reaction support for the loading of the axial pressure simultaneously. The hydraulic oil is arranged and used in conjunction with the resistance wire heating device to control the temperature of the exterior of the rock soil or rock mass sample. During the experiment, the hydraulic oil and the sample are separately hermetically arranged, and isolated without contacting each other. The axial pressure control device is arranged under the pressure chamber base 113 and is configured to provide an axial pressure for the sample to perform uniaxial pressurization test simulation under the set temperature and pressure conditions.

Preferably, the sample 170 is arranged inside the sample encapsulation device 120, and the axis of the sample overlaps with the axis of the test chamber system.

Further, the sample encapsulation device 120 is configured to seal the rock soil or rock mass sample. The adjusting spherical hinge 540 and the top pressure sensor 530 are sequentially arranged above the sample encapsulation device 120. The adjusting spherical hinge is configured to adjust the unevenness of the upper and lower end surfaces of the sample. The pressure sensor is configured to detect an axial force acting on the sample under a load applied by the axial pressure control device. The resistance wire heating spacer block and the pressure chamber base are sequentially arranged under the sample encapsulation device 120. The loading cylinder 511 and the rotating table are sequentially arranged under the outside of the pressure chamber.

Preferably, the sample encapsulation device is arranged vertically.

Preferably, the axis of the axial pressure control device overlaps with the axis of the sample encapsulation device.

Further, the temperature detection device 430 includes a plurality of temperature sensors. The plurality of temperature sensors are separately arranged on the upper part, the bottom part of the sample encapsulation device and the pressure chamber base. The temperature sensors are located and configured to detect the temperatures of different positions in the pressure chamber. According to the detected temperature, the corresponding heating control of the magnetic fluid heating device and the resistance wire heating device is performed to reach the temperature required for the simulation test.

Figure 3:
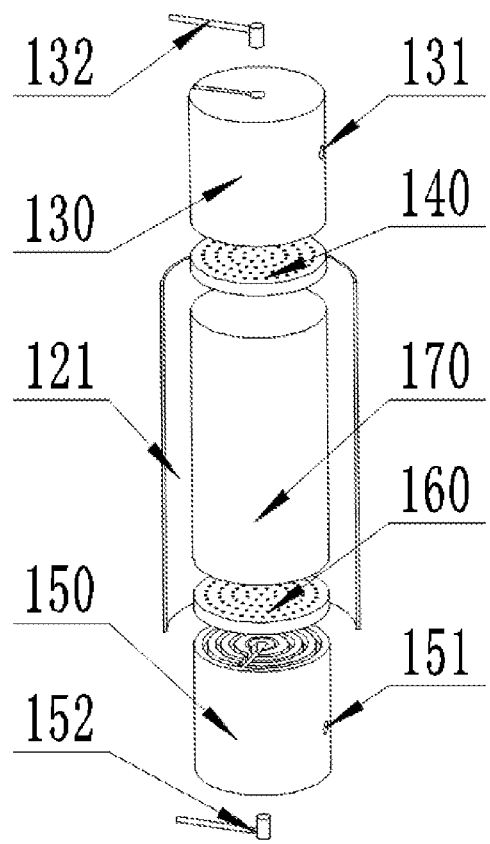
FIG. 3 is a schematic exploded view of the sample encapsulation device in FIG. 1.

Referring to FIGS. 2-3, FIG. 3 is a schematic exploded view of the sample encapsulation device in FIG. 1 and shows only half of the heat shrinkable tube for ease of description. The sample encapsulation device includes the upper spacer block 130, the first permeable spacer block 140, the second permeable spacer block 160, the lower spacer block 150 and the heat shrinkable tube 121. The first permeable spacer block 140 and the upper spacer block 130 are sequentially arranged above the sample 170. The second permeable spacer block 160 and the lower spacer block 150 are sequentially arranged under the sample. The heat shrinkable tube 121 is arranged outside the first permeable spacer block, the sample and the second permeable spacer block. The length of the heat shrinkable tube is greater than the distance between the first permeable spacer block and the second permeable spacer block to achieve the sealing of the sample. The upper and lower regions where the heat shrinkable tube is connected to the upper and lower spacer blocks are hermetically attached to the outer sides of the upper and lower spacer blocks, respectively.

Further, a magnetic fluid injection hole is formed on a side of the upper spacer block 130. The first magnetic fluid channel 131 in fluid communication with the magnetic fluid injection hole is provided inside the upper spacer block 130, and a first groove for receiving the first thermocouple 132 is provided at the upper part of the upper spacer block 130. The magnetic fluid injection hole is in fluid communication with the bottom of the upper spacer block through the first magnetic fluid channel so that the injected magnetic fluid permeates into the sample via the upper spacer block and the first permeable spacer block. A magnetic fluid discharge hole is formed on a side of the lower spacer block 150. The second magnetic fluid channel 151 is provided inside the lower spacer block 150. A second groove for receiving the second thermocouple 152 is provided at the lower part of the lower spacer block 150. The magnetic fluid discharge hole is in fluid communication with the top of the lower spacer block through the second magnetic fluid channel so that the discharged magnetic fluid flows out via the sample, the second permeable spacer block 160, the lower spacer block 150 and the magnetic fluid discharge pipeline. The upper spacer block is in fluid communication with the magnetic fluid loading pump through the magnetic fluid injection pipeline, so that the magnetic fluid is injected into the sample. The lower spacer block is in fluid communication with the magnetic fluid loading pump through the magnetic fluid discharge pipeline, so that the magnetic fluid inside the sample is discharged.

Further, the first groove for receiving the first thermocouple is adjacent to the first magnetic fluid channel provided inside the upper spacer block, and the second groove for receiving the second thermocouple is adjacent to the second magnetic fluid channel provided inside the lower spacer block, so as to further improve the accuracy of the temperature detected by the corresponding thermocouple.

Further, the first permeable spacer block 140 and the second permeable spacer block 160 are each provided with a plurality of through holes for injecting and discharging the magnetic fluid. The first permeable spacer block is arranged between the upper spacer block and the sample, and the second permeable spacer block is arranged between the lower spacer block and the sample, so as to increase the force-bearing area of the end surface of the sample.

Figure 4:
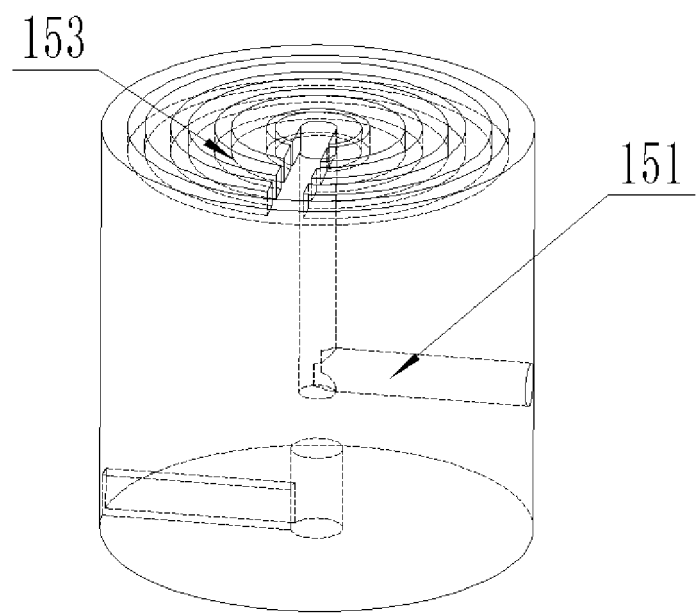
FIG. 4 is a schematic perspective view of the lower spacer block in FIG. 3.

FIG. 4 is a schematic perspective view of the lower spacer block in FIG. 3. That Figure shows the top of the lower spacer block is provided with the permeable groove 153. The permeable groove includes a plurality of circumferential connection structures and an axial connection structure. The axial connection structure passes through the plurality of circumferential connection structures, and the plurality of circumferential connection structures are arranged concentrically at equal intervals to facilitate permeation of the magnetic fluid. The second magnetic fluid channel 151 arranged inside the lower spacer block and the groove for receiving the second thermocouple are arranged without interference with each other. The bottom of the lower spacer block is provided with the groove for receiving the second thermocouple, which is convenient for the system to measure the temperature under the sample.

Further, the positions of the first thermocouple and the second thermocouple can also be arranged to correspond with the first magnetic fluid channel and the second magnetic fluid channel to obtain more accurate temperature generated by the heating of the magnetic fluid inside the sample, thus improving the precise control of the test temperature.

Further, the permeable groove in the upper spacer block is provided at the bottom of the upper spacer block, and has the same structure as that of the permeable groove provided in the lower spacer block.

Figure 5:
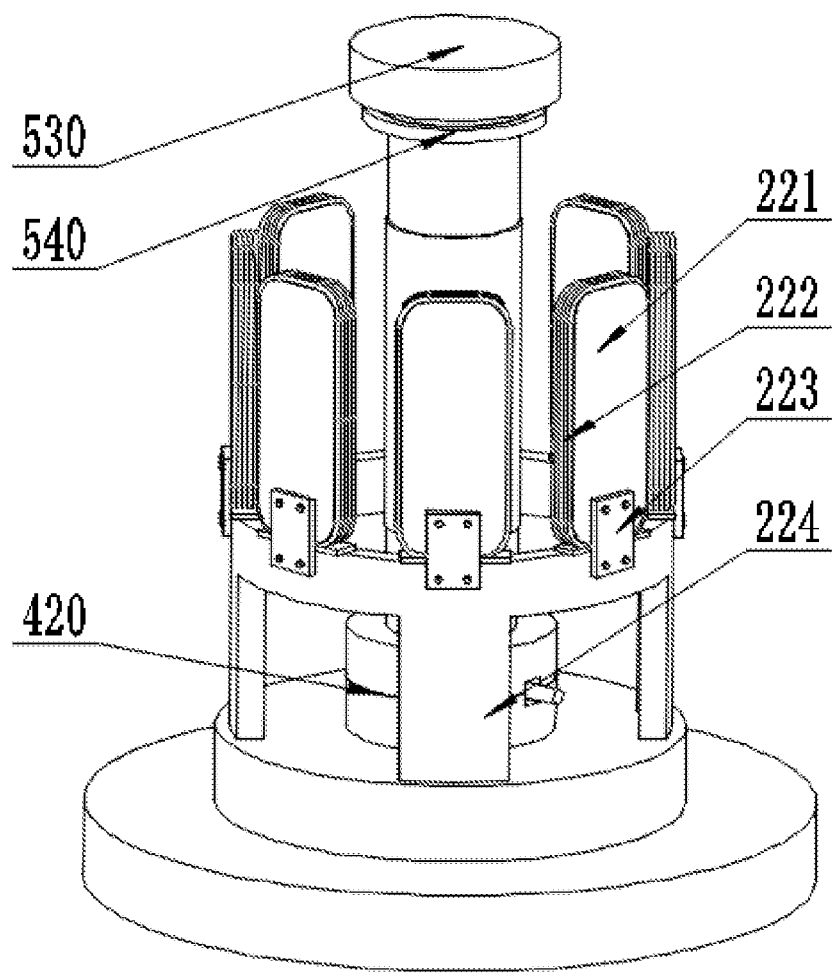
FIG. 5 is a schematic view of part of the structure of the test chamber system in FIG. 1.

Referring to FIG. 5, a schematic view of part of the structure of the test chamber system in FIG. 1. An alternating magnetic field generator is provided on the outside of the sample encapsulation device 120. The alternating magnetic field generator is signally connected to an alternating magnetic field controller arranged externally, and the intensity and frequency of the magnetic field generated in the alternating magnetic field generator is controlled by the alternating magnetic field controller to heat the magnetic fluid injected into the sample.

Further, the alternating magnetic field generator includes a plurality of magnetic cores 221, the supporting base 224, and the coil 222 wound around the magnetic core. The supporting base is fixedly arranged on the top of the pressure chamber base. The plurality of magnetic cores are arranged in an array configuration around the sample encapsulation device. The magnetic core is fixedly arranged on the upper part of the supporting base through the connecting plate 223. In the present embodiment, eight sets of magnetic cores and coils are arranged in an array configuration around the rock mass or rock soil sample. The alternating magnetic field controller outputs the alternating current power to the coil 222 to excite the ferrite in the coil, thereby generating a controllable alternating magnetic field at the position of the sample.

Preferably, the sample encapsulation device is arranged in the center of the alternating magnetic field generator.

Preferably, the central axis of the adjusting spherical hinge 540 and the top pressure sensor 530 sequentially arranged above the sample encapsulation device overlaps with the axis of the sample encapsulation device.

Preferably, the axis of the resistance wire heating spacer block 420 provided under the sample encapsulation device overlaps with the axis of the sample encapsulation device.

Further, the supporting base 224 and the resistance wire heating spacer block 420 are both fixedly arranged on the top of the pressure chamber base.

Further, the supporting base includes a supporting ring and a plurality of supporting legs. The plurality of supporting legs are arranged in an array configuration around the axis of the alternating magnetic field generator, and the supporting ring is arranged on the upper part of the plurality of supporting legs to install the magnetic cores. By arranging the plurality of supporting legs, the size and weight of the alternating magnetic field generator are reduced to reduce the cost while satisfying the load-bearing requirement.

Figure 6:
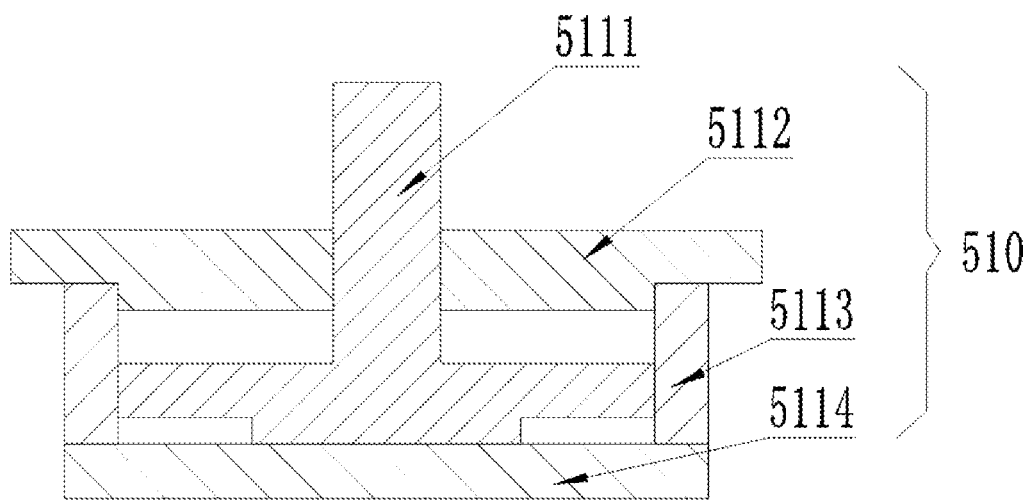
FIG. 6 is a cross-sectional view of the structure of the loading cylinder in FIG. 1.

Referring to FIG. 6, a cross-sectional view of the structure of the loading cylinder in FIG. 1. The loading cylinder is configured to control the axial pressure of the axial pressure control device 510. The loading cylinder includes the loading cylinder end cover 5112, the loading cylinder block 5113, the loading cylinder piston 5111 and the loading cylinder base 5114. The loading cylinder end cover is fixedly arranged under the pressure chamber base, the loading cylinder piston is arranged inside the loading cylinder block, and the loading cylinder piston penetrates the loading cylinder end cover 5112 and the pressure chamber base.

Figure 7:
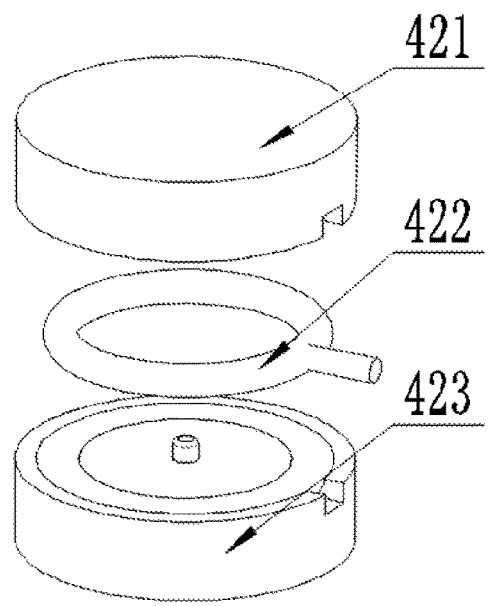
FIG. 7 is a schematic exploded view of the resistance wire heating spacer block in FIG. 1.

Referring to FIG. 7, a schematic exploded view of the resistance wire heating spacer block in FIG. 1. The resistance wire heating device is arranged under the sample encapsulation device. The resistance wire heating device includes a resistance wire heating controller and a resistance wire heating spacer block. The resistance wire heating spacer block includes the upper heating spacer block 421, the thermal resistance wire 422 and the lower heating spacer block 423. The area of the upper heating spacer block is larger than the area of the lower spacer block. The thermal resistance wire is arranged between the upper heating spacer block and the lower heating spacer block, and is connected to the resistance wire heating controller via a wire. The heat generated by the thermal resistance wire is transferred to the upper heating spacer block and the lower heating spacer block, and then the heat is transferred to the hydraulic oil to heat the sample immersed in the hydraulic oil. The resistance wire heating spacer block is configured to heat the hydraulic oil in the pressure chamber to heat the sample in conjunction with the magnetic fluid, thereby improving the heating efficiency.

Further, the bottom of the upper heating spacer block is provided with a groove that is adapted to the shape of the thermal resistance wire, and the top of the lower heating spacer block is also provided with a groove that is adapted to the shape of the thermal resistance wire, so as to facilitate installing the thermal resistance wire. In addition, a protrusion is provided in the middle of the upper part of the lower heating spacer block, and a groove matched with the protrusion is provided in the middle of the lower part of the upper heating spacer block, so that the upper heating spacer block is engaged with the lower heating spacer block.

Figure 8:
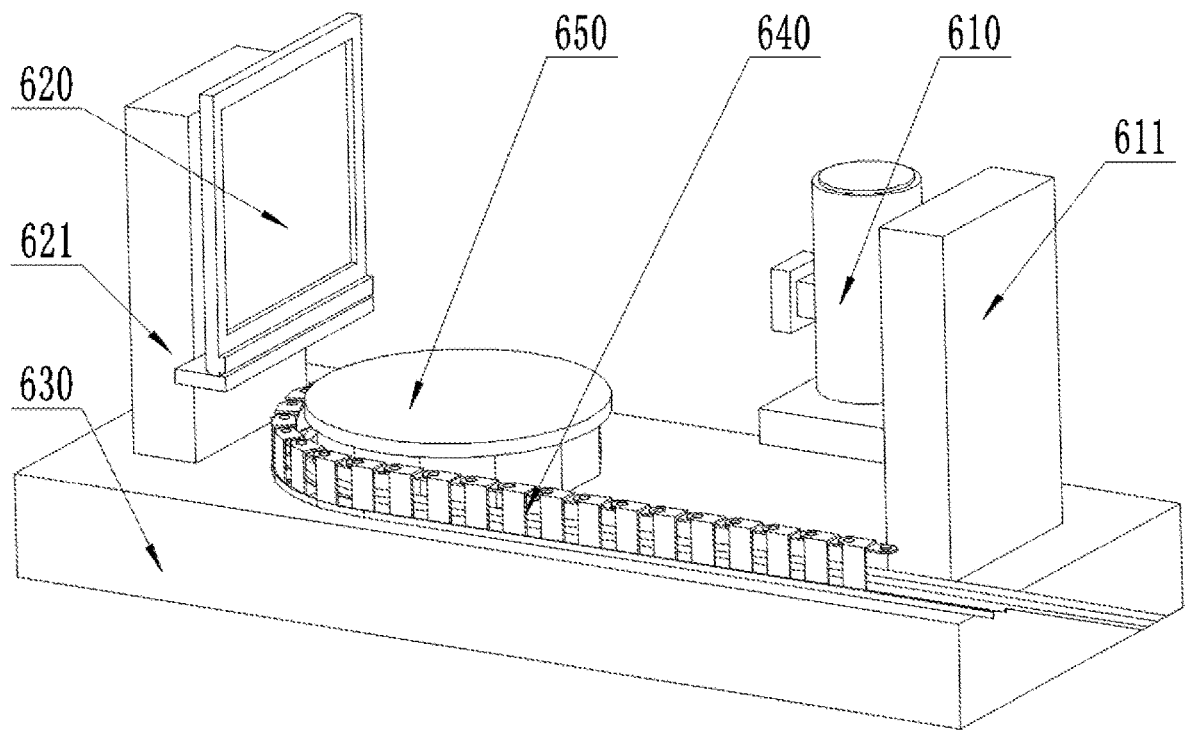
FIG. 8 is a schematic view of a three-dimensional structure of the high-energy accelerator CT detection system in FIG. 1.

Referring to FIG. 8, a schematic view of a three-dimensional structure of the high-energy accelerator CT detection system in FIG. 1. The visible test system further includes the base 630. The test chamber system and the high-energy accelerator CT detection system are both arranged on the upper part of the base. The high-energy accelerator CT detection system includes a ray source device and a detector device. The ray source device and the detector device are separately arranged on both sides of the test chamber system. The ray source device includes the ray source 610 and the ray source stand column 611. The detector device includes the detector 620 and the detector stand column 621. The ray source is arranged on the base through the ray source stand column, and the detector is arranged on the base through the detector stand column. X-rays emitted by the ray source are received by the detector after passing through the rock soil or rock mass sample, and the detector obtains the propagation and development state of fractures and pores inside the rock soil or rock mass sample under the corresponding temperature and pressure adjustments according to the received signal.

It should be noted that the density of the magnetic fluid in the rock soil sample is much greater than that of the rock soil sample. Therefore, CT can identify the location of the magnetic fluid inside the rock soil sample. The position that the magnetic fluid reaches is the location area where the pores and fractures in the rock soil sample are connected. Therefore, this test method can not only detect pores and fractures in the rock soil sample, but also detect the connectivity of the pores and fractures in the rock soil sample (the pores and fractures that the magnetic fluid can reach are connected, and the pores and fractures that the magnetic fluid cannot reach are not connected).

Preferably, the height of each of the ray source and the detector is greater than the height of the test chamber system.

The visible test system further includes a rotating bearing device. The rotating bearing device is arranged under the test chamber system and is configured to drive the test chamber system to rotate. The rotating bearing device includes the rotating table 650 and the drag chain 640, and one end of the drag chain is fixedly arranged on the rotating table. The drag chain is configured to drag the wires and pipelines of the pressure chamber (rotating test machine). A drag chain winding part is provided on the periphery of the rotating table. The drag chain is driven by a power device of the rotating table to wind around the drag chain winding part.

The visible test system further includes a master control device. The master control device is signally connected to the alternating magnetic field controller, the resistance wire heating controller, the temperature detection device, and the axial loading device to store the corresponding data for subsequent calculation of the thermophysical parameters of the rock soil or rock mass.

A visible test method using magnetic fluid to simulate the seepage of rock mass fractures is provided. In this method, the sample encapsulation device is heated by heating magnetic fluid in an alternating magnetic field and the resistance wire heating spacer block, and the devices are provided internally and externally to further improve the uniformity of the heating effect of the rock soil or rock mass sample, thus improving the reliability of the test results.

A rock mass heating method includes the following steps.

Step S100, the sample is encapsulated by a sample encapsulation device and is then placed in the pressure chamber; the sample encapsulation device is formed by the first permeable spacer block and the upper spacer block that are sequentially arranged above the sample, the second permeable spacer block and the lower spacer block that are sequentially arranged under the sample, and a heat shrinkable tube that is arranged outside the first permeable spacer block, the sample and the second permeable spacer block.

Step S200, the sample is in fluid communication with the magnetic fluid loading pump through the magnetic fluid injection pipeline, the upper spacer block, and the first permeable spacer block to form a magnetic fluid injection channel; the sample is in fluid communication with the magnetic fluid loading pump through the magnetic fluid discharge pipeline, the lower spacer block and the second permeable spacer block to form a magnetic fluid discharge channel; and the high-energy accelerator CT detection system is activated to obtain the first state of the sample, that is, the initial state of propagation and development of fractures in the sample in the initial state.

Step S300, hydraulic oil is injected into the pressure chamber until the sample is hermetically encapsulated by the hydraulic oil, to form confining oil to simulate lithostatic confining pressure; the pressure applied to the sample is increased to the set axial pressure value by the axial pressure control device arranged in the axial direction of the sample, to simulate the in-situ stress; the high-energy accelerator CT detection system performs the scanning detection to obtain the second state of the sample, that is, the state of propagation and development of the fractures in the sample under the conditions of confining pressure and axial pressure, to further obtain the state of connectivity between the fractures and pores.

Step S400, the magnetic fluid is injected into the sample through the magnetic fluid injection pipeline, and the third state of the sample is obtained based on the seepage state of the magnetic fluid inside the sample detected by the high-energy accelerator CT detection system or based on a set injection time, wherein the set injection time may be 30 minutes, and the seepage state of the magnetic fluid inside the sample detected by the high-energy accelerator CT detection system may be a state that the magnetic fluid evenly permeates into the fractures in the sample; alternatively, when the magnetic fluid flows out of the lower spacer block, the injection of the magnetic fluid is stopped.

Step S500, based on the third state of the sample, the magnetic fluid is heated through the alternating magnetic field generator arranged externally to heat the interior of the sample in the third state; the confining oil is heated through the resistance wire heating device provided under the sample to heat the exterior of the sample in the third state; and based on temperatures of different positions in the pressure chamber detected by the temperature detection device, the sample is uniformly heated to a set target temperature. The order of heating the sample from the interior of the sample through the alternating magnetic field and heating the sample from the exterior of the sample through heating the hydraulic oil by the resistance wire is not strictly limited, and can be flexibly set as needed.

Further, the visible test system of the present invention further includes a host computer. The host computer is configured to set various parameters, including a current time, a sampling interval, an instrument data group number, high-temperature and high-pressure alarm values, a heating power value, an injection flow quantity of the magnetic fluid loading pump, and a loading pressure of the pressure control system. The host computer is configured to record different temperature changes and pressure loading values in the pressure chamber, and real-time seepage and migration state of the magnetic fluid inside the rock mass sample detected by the high-energy accelerator CT detection system, to obtain the propagation and development process of the fractures inside the rock mass sample and the changes in the connectivity between the fractures and the pores under the corresponding parameters, that is, record each set of data, store the data in the instrument, and store the data in a mobile cloud platform in real time when the mobile network is available. After the data is collected, the host computer (desktop computer) performs the subsequent analysis work to obtain the optimal method for geological body reconstruction, so as to obtain the scheme with maximum connected fractures and pores, and establish the optimal oil and gas migration channel to provide reliable parameters for practical shale oil and gas exploitation.

In the present invention, the high-energy accelerator CT detection system can be used to observe the whole process of rock fracture under high-temperature and high-pressure conditions at present. At this point, or state, the method can obtain the distribution of fractures inside the rock, but it cannot accurately identify the interconnectivity of fractures inside the rock. It is at this state that the magnetic fluid is injected into the rock sample, and the magnetic fluid will enter the interconnected fractures in the process of the rock sample's high-temperature triaxial compression deformation and fracture. Since the density of the magnetic fluid is much greater than that of the rock, the high-energy accelerator CT detection system can identify the distribution of the magnetic fluid in the rock. The fractures that the magnetic fluid reaches are interconnected fractures, and the fractures that the magnetic fluid does not reach are disconnected fractures. During the process of rock fracture, an alternating magnetic field is applied around the rock, which can increase the temperature of the magnetic fluid. In this way, the fluidity and permeability of the magnetic fluid are not only improved, but also the effect of heating the rock from the inside of the rock is achieved.

A visible test method includes the following steps: step S100, the sample is encapsulated by a sample encapsulation device and is then placed in the pressure chamber; the sample encapsulation device is formed by the first permeable spacer block and the upper spacer block that are sequentially arranged above the sample, the second permeable spacer block and the lower spacer block that are sequentially arranged under the sample, and a heat shrinkable tube that is arranged outside the first permeable spacer block, the sample and the second permeable spacer block;

step S200, the sample is in fluid communication with the magnetic fluid loading pump through the magnetic fluid injection pipeline, the upper spacer block, and the first permeable spacer block to form a magnetic fluid injection channel; the sample is in fluid communication with the magnetic fluid loading pump through the magnetic fluid discharge pipeline, the lower spacer block and the second permeable spacer block to form a magnetic fluid discharge channel; and the high-energy accelerator CT detection system is activated to obtain the first state of the sample, that is, the initial state of propagation and development of fractures in the sample in the initial state;

step S300, hydraulic oil is injected into the pressure chamber until the sample is hermetically encapsulated by the hydraulic oil, to form confining oil to simulate lithostatic confining pressure; the pressure applied to the sample is increased to the set axial pressure value by the axial pressure control device arranged in the axial direction of the sample, to simulate the in-situ stress; the high-energy accelerator CT detection system performs the scanning detection to obtain the second state of the sample, that is, the state of propagation and development of the fractures in the sample under the conditions of confining pressure and axial pressure, to further obtain the state of connectivity between the fractures and pores;

step S400, the magnetic fluid is injected into the sample through the magnetic fluid injection pipeline, and the third state of the sample is obtained based on the seepage state of the magnetic fluid inside the sample detected by the high-energy accelerator CT detection system or based on a set injection time, wherein the set injection time may be 30 minutes, and the seepage state of the magnetic fluid inside the sample detected by the high-energy accelerator CT detection system may be a state that the magnetic fluid evenly permeates into the fractures in the sample; alternatively, when the magnetic fluid flows out of the lower spacer block, the injection of the magnetic fluid is stopped;

step S500, based on the third state of the sample, the magnetic fluid is heated through the alternating magnetic field generator arranged externally to heat the interior of the sample in the third state; the confining oil is heated through the resistance wire heating device provided under the sample to heat the exterior of the sample in the third state; and based on temperatures of different positions in the pressure chamber detected by the temperature detection device, the sample is uniformly heated to a set target temperature; wherein the order of heating the sample from the interior of the sample through the alternating magnetic field and heating the sample from the exterior of the sample through heating the hydraulic oil by the resistance wire is not strictly limited, and can be flexibly set as needed;

step S600, after the set target temperature is reached, the temperature, the confining pressure and the pressure of the magnetic fluid are maintained unchanged; after the axial pressure control device increases the axial pressure to a first target value according to a preset pressure gradient, the state of propagation and development of fractures in the sample under different pressures are obtained by the high-energy accelerator CT detection system; if it is detected that the magnetic fluid permeates into the sample completely after an axial pressure is applied, the application of the axial pressure is stopped, and the magnetic fluid is supplemented to continuous to permeates into the sample; the third state of the sample is obtained based on the seepage state of the magnetic fluid inside the sample detected by the high-energy accelerator CT detection system or based on a set injection time, wherein the set injection time may be 30 minutes, and the seepage state of the magnetic fluid inside the sample detected by the high-energy accelerator CT detection system may be a state that the magnetic fluid evenly permeates into the fractures in the sample; alternatively, when the magnetic fluid flows out of the lower spacer block, the injection of the magnetic fluid is stopped; and step S700, based on the preset pressure gradient, step S600 is executed cyclically until the sample is fractured, the states of propagation and development of fractures in the rock mass corresponding to different set parameters are obtained, and the reliable propagation and development process of the connected and disconnected areas of the fractures in the rock sample is obtained, thereby providing reliable test parameters for the reconstruction of reservoir geological bodies in the process of shale oil and gas capture and exploitation.

Although the present invention has been described with reference to the preferred embodiments, various modifications can be made to the present invention and the components thereof can be replaced with equivalents without departing from the scope of the present invention. In particular, as long as there is no structural conflict, the various technical features mentioned in the various embodiments can be combined arbitrarily. The present invention is not limited to the specific embodiments disclosed herein, but includes all technical solutions falling within the scope of the claims.

In the description of the present invention, the terms "center", "upper/above", "lower/under", "left", "right", "vertical", "horizontal", "inner/inside/interior", "outer/outside/exterior", and the like indicating the directional or positional relationships are based on the directional or positional relationships shown in the drawings, and are merely used to facilitate description, rather than indicating or implying that the device or element must have a specific orientation, be configured and operated in a specific orientation, and therefore cannot be construed as a limitation to the present invention. In addition, the terms "first", "second", and "third" are only used for descriptive purposes, and cannot be construed as indicating or implying relative importance.

Furthermore, it should be noted that, in the description of the present invention, unless otherwise clearly defined and limited, the terms "installed", "connected to", and "connection" should be interpreted in a broad sense. For example, with respect to "connection", it can be a fixed connection, a detachable connection, or an integral connection; it can be a mechanical connection or an electrical connection; it can be a direct connection, or an indirect connection through an intermediate medium, and it can be the internal communication between two components. For those skilled in the art, the specific meaning of the above-mentioned terms in the present invention can be understood according to specific implementations.

The term "include/comprise" or any other similar terms are intended to cover non-exclusive inclusion, so that a process, article or equipment/device including a series of elements not only includes those elements, but also includes other elements that are not explicitly listed, or elements inherent in the process, article, or equipment/device.

Hereto, the technical solution of the present invention has been described in conjunction with the preferred embodiments shown in the drawings. However, it is easy for those skilled in the art to understand that the scope of protection of the present invention is not limited to these specific embodiments. Without departing from the principle of the present invention, those skilled in the art can make equivalent modifications or replacements to the relevant technical features, and the technical solutions obtained from these modifications or replacements shall fall within the scope of protection of the present invention.

What is claimed is:

1. A visible test system, comprising
a high-energy accelerator CT detection system,
a test chamber system,
a heating system, and
a pressure control system;
wherein
the high-energy accelerator CT detection system is configured to scan and detect seepage and migration of magnetic fluid in fractures in a sample;
the test chamber system comprises a pressure chamber and a sample encapsulation device, and the sample encapsulation device is immersed in hydraulic oil arranged inside the pressure chamber;
the heating system comprises a magnetic fluid heating device, a resistance wire heating device and a temperature detection device;
wherein the temperature detection device is configured to detect temperatures of different positions in the pressure chamber;
the magnetic fluid heating device comprises a magnetic fluid loading pump and an alternating magnetic field control device;
wherein the magnetic fluid loading pump is configured to supply the magnetic fluid injected into the sample encapsulation device, and
the alternating magnetic field control device is configured to provide an alternating magnetic field for heating the magnetic fluid;
the resistance wire heating device is configured to heat the hydraulic oil inside the pressure chamber to heat the sample inside the sample encapsulation device; and
the pressure control system comprises an axial pressure control device and a confining pressure control device;
wherein the axial pressure control device is configured to provide an axial pressure for the sample inside the sample encapsulation device, and
the confining pressure control device is configured to provide a peripheral pressure for the sample inside the sample encapsulation device.

2. The visible test system according to claim 1, wherein,
the sample encapsulation device comprises an upper spacer block, a first permeable spacer block, a second permeable spacer block, a lower spacer block and a heat shrinkable tube;
wherein the first permeable spacer block and the upper spacer block are sequentially arranged above the sample;
the second permeable spacer block and the lower spacer block are sequentially arranged under the sample;
the heat shrinkable tube is arranged outside the first permeable spacer block, the sample, and the second permeable spacer block; and
a length of the heat shrinkable tube is greater than a distance between the first permeable spacer block and the second permeable spacer block.

3. The visible test system according to claim 2, wherein,
an adjusting spherical hinge and a pressure sensor are sequentially arranged above the sample encapsulation device;
the adjusting spherical hinge is configured to adjust an unevenness of upper and lower end surfaces of the sample; and the pressure sensor is configured to detect an axial force acting on the sample under a load applied by the axial pressure control device.

4. The visible test system according to claim 3, wherein,
the resistance wire heating device is arranged under the sample encapsulation device;
the resistance wire heating device comprises a resistance wire heating controller and a resistance wire heating spacer block;
wherein the resistance wire heating spacer block comprises an upper heating spacer block, a thermal resistance wire and a lower heating spacer block;
wherein an area of the upper heating spacer block is larger than an area of the lower spacer block,
the thermal resistance wire is arranged between the upper heating spacer block and the lower heating spacer block, and
the thermal resistance wire is connected to the resistance wire heating controller via a wire.

5. The visible test system according to claim 4, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

6. The visible test system according to claim 3, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;

a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

7. The visible test system according to claim 2, wherein,
a magnetic fluid injection hole is formed on a side of the upper spacer block;
a first magnetic fluid channel is in fluid communication with the magnetic fluid injection hole and the first permeable spacer block;
the first magnetic fluid channel is arranged inside the upper spacer block;
a magnetic fluid discharge hole is formed on a side of the lower spacer block;
a second magnetic fluid channel is in fluid communication with the magnetic fluid discharge hole and the second permeable spacer block;
the second magnetic fluid channel is arranged inside the lower spacer block;
the upper spacer block is in fluid communication with the magnetic fluid loading pump through a magnetic fluid injection pipeline, and the magnetic fluid is injected into the sample; and
the lower spacer block is in fluid communication with the magnetic fluid loading pump through a magnetic fluid discharge pipeline, and the magnetic fluid inside the sample is discharged.

8. The visible test system according to claim 7, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

9. The visible test system according to claim 2, further comprising a base and a rotating bearing device;

wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

10. The visible test system according to claim 1, wherein, the pressure chamber comprises a pressure chamber end cover, a pressure chamber cylinder, and a pressure chamber base;
wherein the pressure chamber end cover is hermetically arranged at an upper end opening of the pressure chamber cylinder, and the pressure chamber base is hermetically arranged at a lower end opening of the pressure chamber cylinder;
the pressure chamber end cover, the pressure chamber cylinder, the pressure chamber base, and the hydraulic oil arranged inside the pressure chamber cylinder constitute the confining pressure control device; and
the axial pressure control device is arranged under the pressure chamber base, and an axis of the axial pressure control device overlaps with an axis of the sample encapsulation device.

11. The visible test system according to claim 10, wherein,
the axial pressure control device comprises a loading cylinder;
wherein the loading cylinder comprises a loading cylinder end cover, a loading cylinder block, a loading cylinder piston and a loading cylinder base;
wherein the loading cylinder end cover is fixedly arranged under the pressure chamber base;
the loading cylinder piston is arranged inside the loading cylinder block; and
the loading cylinder piston penetrates the pressure chamber base.

12. The visible test system according to claim 11, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

13. The visible test system according to claim 10, wherein,
the alternating magnetic field control device comprises an alternating magnetic field controller and an alternating magnetic field generator;
wherein the alternating magnetic field controller is in communication connection with the alternating magnetic field generator, and the alternating magnetic field controller is configured to control an intensity and a frequency of a magnetic field in the alternating magnetic field generator;
the alternating magnetic field generator comprises a plurality of magnetic cores, a supporting base, and a coil wound around the magnetic core;
wherein the supporting base is fixedly arranged on a top of the pressure chamber base;
the plurality of magnetic cores are arranged in an array configuration around the sample encapsulation device; and
each magnetic core of the plurality of magnetic cores is fixedly arranged on an upper part of the supporting base through a connecting plate.

14. The visible test system according to claim 13, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;

the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

15. The visible test system according to claim 10, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

16. The visible test system according to claim 1, further comprising a base and a rotating bearing device;
wherein the test chamber system and the high-energy accelerator CT detection system are both arranged on an upper part of the base;
the high-energy accelerator CT detection system comprises a ray source device and a detector device;
wherein the ray source device and the detector device are separately arranged on both sides of the test chamber system;
the ray source device comprises a ray source and a ray source stand column;
the detector device comprises a detector and a detector stand column;
wherein the ray source is arranged on the base through the ray source stand column, and
the detector is arranged on the base through the detector stand column;
a height of each of the ray source and the detector is greater than a height of the test chamber system;
the rotating bearing device is arranged under the test chamber system, and the rotating bearing device is configured to drive the test chamber system to rotate;
the rotating bearing device comprises a rotating table and a drag chain, and one end of the drag chain is fixedly arranged on the rotating table;
a drag chain winding part is provided on a periphery of the rotating table; and
the drag chain is driven by a power device of the rotating table to wind around the drag chain winding part.

17. A rock mass heating method, comprising:
step S100, encapsulating a sample by a sample encapsulation device;
step S200, constructing first fluid communication between the sample and a magnetic fluid loading pump through a magnetic fluid injection pipeline, an upper spacer block, and a first permeable spacer block to form a magnetic fluid injection channel; and
constructing second fluid communication between the sample and the magnetic fluid loading pump through a magnetic fluid discharge pipeline, a lower spacer block, and a second permeable spacer block to form a magnetic fluid discharge channel;
activating a high-energy accelerator CT detection system to obtain a first state of the sample;
step S300, injecting hydraulic oil into a pressure chamber until the sample is hermetically encapsulated by the hydraulic oil, to form confining oil to simulate a lithostatic confining pressure;
increasing a pressure applied to the sample to a set axial pressure value by an axial pressure control device arranged in an axial direction of the sample to simulate an in-situ stress;
obtaining a second state of the sample based on scanning detection of the high-energy accelerator CT detection system;
step S400, injecting magnetic fluid into the sample in the second state through the magnetic fluid injection pipeline, and obtaining a third state of the sample based on a seepage state of the magnetic fluid inside the sample or based on a set injection time, wherein the seepage state of the magnetic fluid is detected by the high-energy accelerator CT detection system;
step S500, heating the magnetic fluid through an alternating magnetic field generator arranged externally to heat an interior of the sample in the third state;
heating the confining oil through a resistance wire heating device provided under the sample to heat an exterior of the sample in the third state; and
based on temperatures of different positions in the pressure chamber, uniformly heating the sample to a set target temperature, wherein the temperatures of the different positions in the pressure chamber are detected by a temperature detection device.

* * * * *